United States Patent
Noe et al.

[11] Patent Number: 5,929,253
[45] Date of Patent: Jul. 27, 1999

[54] L-ASPARTYL-L-THIENYLALANINE METHYL ESTER, PROCESS FOR ITS PREPARATION AND USE AS SWEETENER

[75] Inventors: Christian Noe, Frankfurt; Antje Weigand-Becker, Aachen, both of Germany

[73] Assignee: Pharmacon Forschung und Beratung GmbH, Scharding, Austria

[21] Appl. No.: 08/978,577

[22] Filed: Nov. 26, 1997

Related U.S. Application Data

[63] Continuation of application No. PCT/NL96/00207, May 22, 1996.

[30] Foreign Application Priority Data

May 26, 1995 [AT] Austria ........................................ 886/95

[51] Int. Cl.⁶ .......................... C07D 333/22; A61K 31/38
[52] U.S. Cl. ............................................. 549/76; 514/438
[58] Field of Search ................................ 549/76; 514/438

[56] References Cited

U.S. PATENT DOCUMENTS

| | | | |
|---|---|---|---|
| 4,454,328 | 6/1984 | Brennan et al. | 549/28 |
| 4,692,513 | 9/1987 | Blum et al. | 530/801 |
| 5,286,509 | 2/1994 | D'Angelo et al. | 426/548 |
| 5,723,651 | 3/1998 | Hijiya et al. | 560/169 |

*Primary Examiner*—Deborah C. Lambkin
*Attorney, Agent, or Firm*—IP Group of Pillsbury Madison & Sutro LLP

[57] ABSTRACT

L-aspartyl-L-thienylalanine methyl esters of the formula

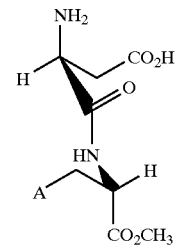

where A is a radical of the formula

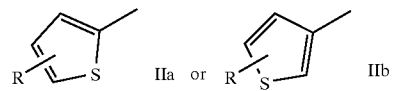

in which R can be H or $CH_3$, a process for its preparation, and its use as sweetener.

4 Claims, No Drawings

L-ASPARTYL-L-THIENYLALANINE METHYL ESTER, PROCESS FOR ITS PREPARATION AND USE AS SWEETENER

This is a Continuation of International Appl No. PCT/NL96/00207 filed May 22, 1996 which designated the U.S.

Artificial sweeteners are used in a multiplicity of foods, saccharin, cyclamate, acesulfame-K and aspartame being amongst the most well known artificial sweeteners used. However, the use of saccharin and cyclamate has continued to cause discussion with respect to their hazard to health and has thus led to development of novel sweeteners having high sweetening power. Thus, most recently, the sweeteners aspartame and acesulfame-K are becoming increasingly more widespread as food additives, as a result of which numerous studies have been carried out on their properties and applications. Since acesulfame-K does not approach aspartame with respect to its taste qualities, aspartame is the better known and more frequently used artificial sweetener. However, since some individuals cannot tolerate the intake of aspartame, for example in the case of metabolic disorders associated with phenylalanine, the real solution to problems in the area of artificial sweeteners is still the development of novel products which are well tolerated and have a high sweetening power. The object of the present invention was therefore to find compounds which do not have the disadvantages of the previously known sweeteners and which, in comparison with the prior art, have the same or higher sweetening power. The prior art, for example J. Med. Chem. 1990, 33, pages 1676–1682, discloses compounds, for example, in which the phenylalanine group of aspartame has been replaced. In this study, 8 L-aspartyl dipeptides derived from heterocyclic glycine esters were prepared and studied. However, it was found in this case that the β-thienylalanine fenchyl ester compounds (compound 14) have no sweetening power.

Unexpectedly, compounds have now been found in which the phenylalanine group of aspartame is replaced by a thienylalanine group and which have, in comparison with aspartame, increased, or at least equally high, sweetening power.

The present invention therefore relates to L-aspartyl-L-thienylalanine methyl esters of the formula

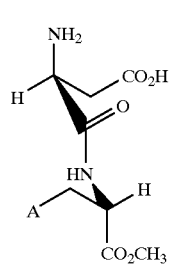

I where A is a radical of the formula

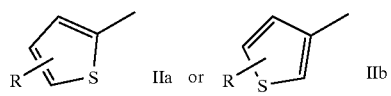

IIa or IIb in which R can be H or CH₃.

A in the formula I is thus a radical of the formula IIa or IIb which can optionally be substituted by a methyl radical.

Examples thereof are 2'-thienyl, 3'-thienyl, 2'-(5'-methyl)thienyl, 2'-(4'-methyl)thienyl or 3'-(5'-methyl)thienyl. Preferably, X is a 2'-thienyl, 3'-thienyl or 2'-(5'-methyl) thienyl radical.

The compounds according to the invention can be prepared by a chemical or enzymatic route. Preferably, conventional chemical processes are employed. Thus, for example, L-aspartic acid, whose α-amino group and β-carboxyl group are protected, is converted, by activating the α-carboxyl group, into a reactive derivative which is condensed with the hydrochloride of the corresponding thienylalanine compound, whereupon, subsequently to the condensation, the protecting groups are removed.

Preferred protecting groups in this case are, for the amino function for example, the benzyloxycarbonyl group (Z) or the tert-butyloxycarbonyl group (Boc), or, for the β-carboxyl group, the tert-butyl radical (t-Bu). Both protecting groups can then be removed in one step acidolytically (HBr/CH₃COOH or HF).

However, instead of the abovementioned protecting groups and methods of removal, other protecting groups or methods of removal known from the prior art of peptide syntheses can be used.

The α-carboxyl group can likewise be activated by a method known from the prior art, for example by the azide method, the mixed anhydride method, the active ester method or the carbodiimide method.

To prepare the compounds according to the invention, the α-carboxyl group of the L-aspartic acid whose α-amino group and β-carboxyl group are protected, for example the α-carboxyl group of (S)-N-benzyloxycarbonylaspartic acid β-tert-butyl ester, is thus first activated, for instance by reaction with trichlorophenol in the presence of dicyclohexylcarbodiimide (DCC). For this purpose, a solution of aspartic acid and trichlorophenol, which is preferably used in a slight excess, is admixed with DCC at +10 to −10° C. and stirred for 2 to 10 hours. A suitable solvent here is, for example, ethyl acetate. The mixture is then heated to about 15 to 30° C., further stirred for 5 to 30 minutes, the precipitated urea is filtered off, washed repeatedly with ethyl acetate and the filtrate is freed from solvent in vacuo. The residual oil is then flash-chromatographed on silica gel using a petroleum ether/ether mixture.

The starting material for this reaction step, (S)-N-benzyloxycarbonylaspartic acid β-tert-butyl ester, can be prepared, for example, in a similar manner to that of E. Wünsch, A. Zwick, Z. physiol. Chem. 328 (1962) 235.

Coupling to the hydrochloride of the corresponding thienylalanine compound is then carried out in the presence of an acid acceptor, such as triethylamine, pyridine, etc.

Preferably, here, the product obtained in the preceding step is dissolved in a suitable anhydrous solvent, such as DMF, and further stirred with the hydrochloride compound for a plurality of days, preferably 2 to 5 days, at +5 to −10° C. in the presence of the acid acceptor.

The coupled product is preferably isolated by extraction, for example with ether and ice-water, drying the organic phase, for instance by sodium sulphate or magnesium sulphate, and distilling off the solvent. The flash chromatography on silica gel then follows. The hydrochloride of (S)-3-(2'-thienyl)alanine methyl ester is disclosed, for example, by J. Dunn. J. biol. Chem. 234 (1959), p. 802; (S)3-(3'-thienyl)alanine is described, for example, in K. Dittmer et al., J. Am. Chem. Soc. 71 (1949) p. 1201.

After the coupling step, the protecting group is removed, for instance by adding HBr and glacial acetic acid, whereupon the end product which is wanted can be isolated in salt form.

The protecting group is removed here at a temperature of 15 to 30° C., preferably at room temperature, with dropwise addition of a solution of HBr in glacial acetic acid to a glacial acetic acid solution of the product obtained in the preceding step, with stirring for 1 to 4 hours.

The solvents are then distilled off, the residue is taken up in ether or dioxane, and the product precipitating out is filtered off and dried in vacuo. In order to isolate the desired end product from the hydrobromide thus obtained, the hydrobromide compound is dissolved in water and admixed with a base, for example with a basic ion exchanger, for example Amberlite, and stirred at 30 to 60° C. for 10 to 60 minutes. The solid is then filtered off, washed with water and the eluate and the washing solution concentrated in vacuo to the extent that the appropriate end product precipitates out, which is then filtered off and dried.

The present invention therefore further relates to a process for preparing compounds of the formula

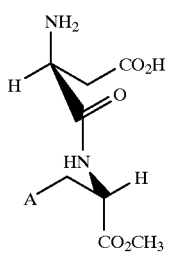

I where A is a radical of the formula

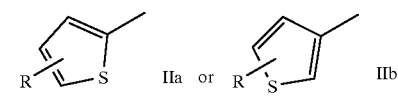

in which R can be H or CH$_3$, which is characterized in that a compound of the formula

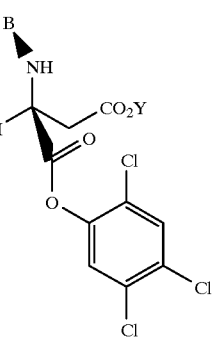

III where B is an amino protecting group and Y is a carboxyl protecting group, is reacted with a compound of the formula

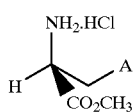

IV where A has the above meaning, in the presence of an acid acceptor, to give a compound of the formula

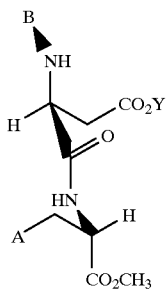

V where B and Y have the above meaning, whereupon, after removing protecting groups by the acidolytic method, the corresponding compound of the formula I is isolated using a base from the salt thus produced.

The compounds according to the invention of the formula I are distinguished by, in comparison with the prior art, improved or equally high sweetening capacity, even in the case of addition of very small amounts, and are therefore suitable for use as artificial sweetener.

The present invention therefore further relates to the use of compounds of the formula

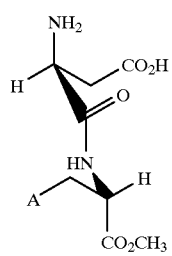

I where A is a radical of the formula

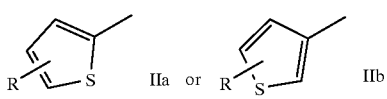

in which R can be H or CH$_3$ as artificial sweetener.

EXAMPLE 1

Preparation of α-aspartyl-L-(2-thienyl)alanine, methyl ester (1)

1.1. (S)-N-Benzyloxycarbonylaspartic acid α-tert-butyl-α-2,4,5-trichlorophenyl ester (4)

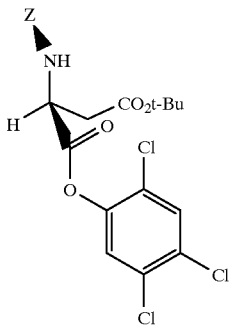

A solution of 7.5 g (23.2 mmol) of (S)-N-benzyloxycarbonylaspartic acid β-tert-butyl ester and 5.05 g (25.6 mmol) of trichlorophenol in 60 ml of ethyl acetate was admixed with 4.74 g (23.3 mmol) of DCC at 0° C. and stirred for 4 h in an ice bath. After stirring for a further 15 minutes at room temperature, the precipitated urea was filtered off, washed repeatedly with ethyl acetate and the filtrate was freed from solvent in vacuo. The residual oil was flash-chromatographed on 260 g of silica gel using petroleum ether (40–60° C.)/ether (gradient from 9:1 to 7:3).

Yield: 8.3 g (71%), colourless oil $R_f$=0.28 (petroleum ether:ether=9:1) $[\alpha]^{23}_D$=–6° C., (c=1.0, $CH_2Cl_2$)

$^1$H-NMR ($CDCl_3$): δ=7.56 (s; 1H, CH), 7.42–7.32 (m; 6H, $C_6H_5$, CH), 5.91 (d; 1H, NH), 5.18 (s; 2H, $OCH_2$), 4.92 (m; 1H, CH), 3.14 (dd; 1H, CH of —$CH_2$—), 2.92 (dd; 1H, CH of —$CH_2$—), 1.48 (s; 9H, $CH_3$).

$^{13}$C-NMR ($CDCl_3$): δ=169.87 (s; COO), 168.39 (s; COO), 155.97 (s; CONH), 145.44 (s; C), 135.99 (s; C), 131.55 (s; C), 130.87 (d; CH), 128.56 (d; CH), 128.29 (d; CH), 128.13 (d; CH), 125.86 (s; C), 125.11 (d; CH), 82.40 (s; OC), 67.36 (t; $OCH_2$) 50.58 (d; CH), 37.68 (t; —$CH_2$—), 28.03 (q; $CH_3$).

1.2. L-β-tert-Butyl-N-carbobenzoxy-α-aspartyl-L-(2-thienyl)alanine; methyl ester (5)

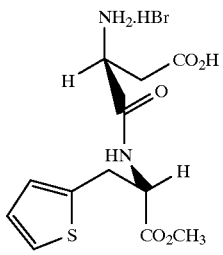

8.0 g (15.91 mmol) of 4 are dissolved in 50 ml of anhydrous DMF and are admixed at 0° C. with 3.53 g (15.91 mmol) of (S)-3-C2'-thienyl)alanine, methyl ester, hydrochloride and 2.20 ml (15.91 mmol) of triethylamine and stirred for 3 days at 0–4° C. The reaction solution was then partitioned between ice-water and ether, the aqueous phase was extracted repeatedly with ether, the combined organic phases were dried with sodium sulphate and the solvent was distilled off. The crude product thus obtained was flash-chromatographed on 220 g of silica gel using petroleum ether:ether (gradient from 6:4 to 1:2).

Yield: 5.7 g (73%), colourless solid, m.p.: 56–57° C. $R_f$=0.36 (petroleum ether:ether=1:2), $[\alpha]^{25}_D$=+41.5°, (c=0.89, $CH_2Cl_2$)

$^1$H-NMR ($CDCl_3$): δ=7.30–7.25 (m; 5H, $C_6H_5$), 7.07 (dd; 1H, Th-H-3), 7.02 (bs; 1H, CONH), 6.85 (dd; 1H, Th-H-4), 6.78 (dd; 1H, Th-H-5), 5.90 (d; 1H, CONH), 5.06 (s; 2H, $OCH_2$), 4.77 (m; 1H, CH), 4.50 (m; 1H, CH), 3.67 (s; 3H, $OCH_3$), 3.28 (m; 2H, —$CH_2$—), 2.85 (dd; 1H, CH of —$CH_2$—), 2.55 (dd; 1H, CH of —$CH_2$—), 1.36 (s; 9H, $CH_3$).

$^{13}$C-NMR ($CDCl_3$): δ=170.99 (s; CO), 170.81 (s; CO), 170.31 (s; CO), 156.51 (s; CONH), 137.02 (s; C), 136.08 (s; C), 128.06 (d; CH), 128.23 (d; CH), 128.06 (d; CH), 127.07 (d; CH), 126.99 (d; CH), 124.86 (d; CH), 81.82 (s; OC), 67.21 (t; $OCH_2$), 53.35 (q; $OCH_3$), 52.45 (d; CH), 51.09 (d; CH), 37.28 (t; —$CH_2$—), 31.85 (t; —$CH_2$—), 27.99 (q; $CH_3$).

$C_{24}H_{30}N_2O_7S$ (490.58): Calculated: C 58.76 H 6.16 N 5.71 Found: C 58.55 H 6.12 N 5.66

1.3. N-L-α-Aspartyl-L-(2-thienyl)alanine, methylester, hydrobromide (6)

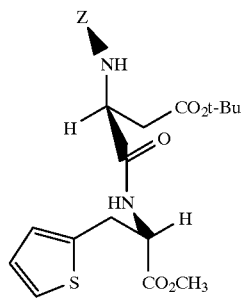

A solution of 5.0 g (10.2 mmol) of 5 in 20 ml of glacial acetic acid was admixed dropwise at room temperature with 15 ml (61.2 mmol) of a 4.1M (33%) solution of HBr in glacial acetic acid and the mixture was stirred for 2 h.

The solvents were distilled off in a water-jet vacuum and the oily residue was digested with 100 ml of ether. In the course of this, a colourless crystalline powder precipitated out, which was filtered off and dried in vacuo.

Yield: 3.6 g (93%), colourless needles, m.p.: 45–46° C. $R_f$=0.30 (EtOAc:MeOH=1:1), $[\alpha]^{25}_D$=–1.97° (c=1.17, $H_2O$)

$^1$H-NMR ($D_2O$): δ=7.30 (dd; 1H, Th-H-3), 6.98 (dd; 1H, Th-H-4), 6.70 (dd; 1H, Th-H-5), 4.72 (m; 1H, CH), 4.30 (m; 1H, CH), 3.72 (s; 3H, $OCH_3$), 3.43 (dd; 1H, CH of —$CH_2$—), 3.33 (dd; 1H, CH of —$CH_2$—), 2.97 (m; 2H, —$CH_2$—), 1.36 (s; 9H, $CH_3$).

$^{13}$C-NMR ($D_2O$:$d_6$-DMSO=7:1): δ=173.73 (s; COO), 169.68 (s; COO), 139.39 (s; C), 128.90 (d; CH), 128.63 (d; CH), 126.87 (d; CH), 55.91 (d; CH), 54.53 (q; $OCH_3$), 50.67 (d; CH), 36.27 (t; —$CH_2$—), 31.95 (t; —$CH_2$—)

$C_{12}H_{17}BrN_2O_5S$ (381.25): Calculated: C 37.81 H 4.49 N 7.35 Found: C 38.09 H 4.81 N 7.19

1.4. Preparation of N-L-α-aspartyl-L-(2-thienyl)alanine, methyl ester (1)

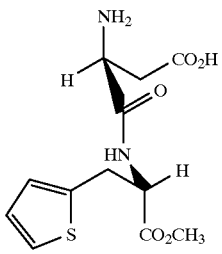

20 ml of a strongly basic ion exchanger (Amberlite IRA-400) were stirred overnight in saturated aqueous sodium acetate solution. The ion exchanger was then filtered off and washed to neutrality with water.

The Amberlite thus activated was stirred for 30 min at 45° C. with a solution of 3.1 g (8.10 mmol) of 6 in 50 ml of water. The solid was filtered off, washed with 30 ml of water, and the eluate and the washing solutions were highly concentrated in vacuo. On cooling, colourless needles precipitated out which were filtered off and dried.

Yield: 1.8 g (74%), colourless needles, m.p.: 223–225° C. $R_f$=0.405 (EtOAc:MeOH=1:1), $[\alpha]^{23}_D$=+43° (c=0.71, HOAc)

$^1$H-NMR (D$_2$O): δ=7.28 (dd; 1H, Th-H-3), 6.96 (dd; 1H, Th-H-4), 6.88 (dd; 1H, Th-H-5), 4.69 (m; 1H, CH), 4.15 (m; 1H, CH), 3.69 (s; 3H, OCH$_3$), 3.40 (dd; 1H, CH of —CH$_2$—), 3.28 (dd; 1H, CH of —CH$_2$—), 2.71 (dd; 1H, CH of —CH$_2$—), 2.60 (dd; 1H, CH of —CH$_2$—).

$^{13}$C-NMR (d$_6$-DMSO) δ=172.29 (s; CO), 170.97 (s; CO), 170.70 (s; CO), 138.44 (s; C), 127.00 (d; CH), 126.70 (d; CH), 124.92 (d; CH), 53.70 (q; OCH$_3$), 52.15 (d; CH), 50.48 (d; CH), 37.41 (t; —CH$_2$—), 30.82 (t; —CH$_2$).

C$_{12}$H$_{16}$N$_2$O$_5$S (300.33): Calculated: C 47.99 H 5.37 N 9.21 Found: C 47.70 H 5.60 N 9.33

EXAMPLE 2

Preparation of N-L-α-aspartyl-L-(3-thienyl)alanine, methyl ester (2)

2.1. (S)-3-(3'-Thienyl)alanine, methyl ester, hydrochloride (7)

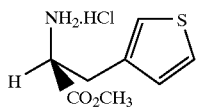

A vigourous stream of anhydrous hydrogen chloride was passed at room temperature for 3 h through a suspension of 4.00 g (23.4 mmol) of (S)-3-(3'-thienyl)alanine in 150 ml of anhydrous methanol.

The solvent was then evaporated to dryness, the residue was taken up in 20 ml of methanol and admixed with ether until precipitation was complete. The precipitated product was filtered off and dried.

Yield: 4.6 g (89%), brown solid, m.p.: 174–176° C. $[\alpha]^{23}_D$=+5.3° (c=0.76, MeOH)

$^1$H-NMR (D$_2$O): δ=7.41 (dd; 1H, Th-H-4), 7.22 (d; 1H, Th-H-2), 6.93 (d; 1H, Th-H-5), 4.35 (t; 1H, α-CH), 3.77 (s; 3H, OCH$_3$), 3.25 (d; 2H, —CH$_2$—).

$^{13}$C-NMR (D$_2$O): δ=172:6 (s; COO), 136.1 (s; C), 130.6, 130.1, 127.4 (d; C), 56.2 (d; α-CH), 56.1 (q; OCH$_3$), 32.5 (t; —CH$_2$—).

2.2. L-β-tert-Butyl-N-carbobenzoxy-α-aspartyl-L-(3-thienyl)alanine, methyl ester (8)

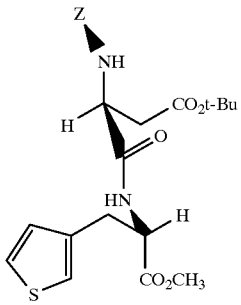

6.8 g (13.5 mmol) of 4 were dissolved in 50 ml of anhydrous DMF, admixed at 0° C. with 3.00 g (13.5 mmol) of 7 and 1.87 ml (13.5 mmol) of triethylamine and the mixture was stirred for 3d at 0–4° C.

The reaction solution was then partitioned between 160 ml of ice-water and 100 ml of ether, the aqueous phase was repeatedly extracted with ether and the combined organic phases were washed with saturated sodium chloride solution. The ether solution was dried with sodium sulphate and the solvent was distilled off. The crude product thus obtained was flash-chromatographed on 220 g of silica gel using petroleum ether:ether (gradient from 6:4 to 1:2).

Yield: 5.2 g (79%), colourless solid, m.p.: 74–76° C. $R_f$=0.364 (petroleum ether:ether=1:2), $[\alpha]^{25}_D$=+31.2°, (c=1.1, CH$_2$Cl$_2$)

$^1$H-NMR (CDCl$_3$): δ=7.30–7.25 (m; 5H, C$_6$H$_5$), 7.18 (m; 1H, Th-H), 6.98 (m; 1H, Th-H), 6.82 (m; 1H, Th-H), 5.90 (d; 1H, CONH), 5.06 (s; 2H, OCH$_2$), 4.73 (m; 1H, a-CH), 4.50 (m; 1H, α-CH), 3.66 (s; 3H, OCH$_3$), 3.08 (m; 2H, —CH$_2$—), 2.85 (dd; 1H, CH of —CH$_2$—), 2.50 (dd; 1H, CH of —CH$_2$—), 1.36 (s; 9H, CH$_3$).

$^{13}$C-NMR (CDCl$_3$): δ=171.26 (s; CO), 171.07 (s; CO), 170.19 (s; CO), 155.89 (s; CONH), 136.01 (s; CH), 135.69 (s; C-3-Th), 128.49 (d; CH), 128.22 (d; CH), 128.17 (d; CH), 127.07 (d; CH), 125.86 (d; CH), 122.89 (d; CH), 81.76 (s; OC$_{quart}$), 67.15 (t; OCH$_2$), 52.88 (q; OCH$_3$), 52.25 (d; α-CH), 50.97 (d; α-CH), 37.15 (t; —CH$_2$), 32.12 (t; —CH$_2$—), 27.93 (q; CH$_3$).

2.3. N-L-α-Aspartyl-L-(3-thienyl)alanine, methyl ester, hydrobromide (9)

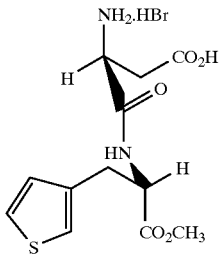

A solution of 5.0 g (10.2 mmol) of 8 in 50 ml of glacial acetic acid was admixed dropwise at room temperature with 15 ml (61.2 mmol) of a 4.1M (33%) solution of HBr in glacial acetic acid and the mixture was stirred for 2 h.

The solvents were then distilled off in a water-jet vacuum and the oily residue was digested with 100 ml of ether. In the course of this, a colourless crystalline powder precipitated out, which was filtered off and dried in vacuo.

Yield: 3.7 g (95%), colourless needles, m.p.: 82–84° C. $R_f$=0.371 (EtOAc:MeOH=1:1), $[\alpha]^{25}_D$=+27° (c=1.0, HOAc)

¹H-NMR (D₂O): δ=7.39 (m; 1H, Th-H), 7.18 (m; 1H, Th-H), 6.98 (m; 1H, Th-H), 4.74 (m; 1H, α-CH), 4.28 (m; 1H, α-CH), 3.70 (s; 3H, OCH₃), 3.22 (dd; 1H, CH of —CH₂—), 3.15 (dd; 1H, CH of —CH₂—), 2.95 (m; 2H, —CH₂—).

¹³C-NMR (D₂O): δ=172.13 (s; COO), 171.84 (s; COO), 167.63, (s; CON-H), 137.30 (s; C-3-Th), 127.55 (d; CH), 125.87 (d; CH), 122.56 (d; CH), 54.43 (d; α-CH), 53.54 (q; OCH₃), 49.79 (d; α-CH), 35.31 (t; —CH₂—), 31.21 (t; —CH₂—).

C₁₂H₁₇BrN₂O₅S.0.40 H₂O (388.46): Calculated: C 37.10 H 4.62 N 7.21 Found: C 37.15 H 4.70 N 7.08

2.4. N-L-α-Aspartyl-L-(3-thienyl)alanine, methyl ester (2)

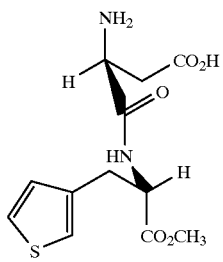

20 ml of strongly basic ion exchanger (Amberlite IRA-400) were stirred overnight in saturated aqueous sodium acetate solution. The ion exchanger was then filtered off and washed to neutrality with water.

The Amberlite thus activated was stirred with a solution of 3.5 g (9.20 mmol) of 9 in 50 ml of water for 30 min at 45° C. The solid was filtered off, washed with 30 ml of water, digested once more at 45° C. with 50 ml of water and the eluate, and also the scrubbing solutions were greatly concentrated in vacuo. On cooling, colourless needles precipitated out, which were filtered off and dried.

Yield: 2.3 g (83%), colourless needles, 234–235° C. R_f=0.408 (EtOAc:MeOH=1:1), [α]²³_D=+30° (c=1.0, HOAc)

¹H-NMR (D₂O): δ=7.39 (m; 1H, Th-H), 7.17 (m; 1H, Th-H), 7.00 (m; 1H, Th-H), 4.70 (m; 1H, α-CH), 4.16 (m; 1H, α-CH), 3.70 (s; 3H, OCH), 3.20 (dd; 1H, CH of —CH₂—), 3.11 (dd; 1H, CH of —CH₂—), 2.72 (dd; 1H, CH of —CH₂—), 2.64 (dd, 1H, CH of —CH₂—).

¹³C-NMR (D₂O): δ=178.46 (s; CO), 175.68 (s; CO), 172.03, (s; CO) 139.08 (s; C-3-Th), 130.92 (d; CH), 129.20 (d; CH), 125.91 (d; CH), 56.55 (q; OCH₃), 55.69 (d; α-CH), 53.14 (d; α-CH), 39.57 (t; —CH₂—), 33.50 (t; —CH₂—).

C₁₂H₁₆N₂O₅S.0.70 H₂O (312.95): Calculated: C 46.06 H 5.60 N 8.95 Found: C 46.06 H 5.53 N 8.81

EXAMPLE 3

N-L-α-Aspartyl-(L-[2-(5-methyl)thienyl]alanine, methyl ester (3)

3.1. 2-Hydroxymethyl-5-methylthiophene (10)

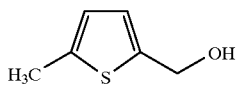

A solution of 50 ml (456 mmol) of 5-methylthiophene-2-carbaldehyde in 350 ml of ethanol was admixed with 13.2 g (347 mmol) of sodium borohydride a little at a time, with ice cooling and stirring. After addition was complete, the mixture was further stirred for another 2 h and the reaction solution was then poured into a mixture of 400 g of ice and 200 ml of saturated ammonium chloride solution. After gas formation was complete, the solution was freed from ethanol in vacuo. The aqueous residue was extracted repeatedly with ether, the combined ether phases were washed with saturated sodium chloride solution and dried over sodium sulphate. The solvent was distilled off. An oily residue remained behind which was distilled at a pressure of 20 mbar.

1st fraction: 55–100° C. 0.3 g

2nd fraction: 101–99° C. 50.0 g

The product was unstable even when stored in a refrigerator, and should therefore be reacted as soon as possible.

Yield: 50.3 g (86%), colourless liquid R_f=0.512 (petroleum ether:ether=1:1).

¹H-NMR (CDCl₃): δ=6.81 (d; 1H, CH), 6.63 (d; 1H, CH), 4.74 (s; 2H, —CH₂—), 2.50 (s; 3H, CH₃), 1.75 (bs; 1H, OH).

¹³C-NMR (CDCl₃): δ=141.70 (s; C), 140.24 (s; C), 125.54 (d; C), 124.82 (d; C), 59.86 (t; CH2), 15.39 (q; CH₃).

3.2. 2-Bromomethyl-5-methylthiophene (11)

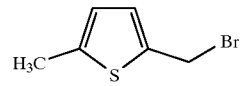

30 g (234 mmol) of 10 in 300 ml of anhydrous ether were admixed with a solution of 149 g (550 mmol) of phosphorous tribromide in 350 ml of anhydrous ether in the course of 90 min, with ice cooling. After stirring for 2 h at room temperature, the reaction solution was poured onto 2 kg of ice and the organic phase was separated off.

The aqueous phase was saturated with sodium chloride and extracted repeatedly with ether. The combined organic phases were dried with sodium sulphate and the solvent was evaporated off in a low vacuum.

Yield: 38 g (95%), brown liquid.

The product has a strong tendency to polymerize, and should therefore not be heated, and should be isolated as far as possible under an inert atmosphere or further processed immediately.

¹H-NMR (CDCl₃): δ=6.85 (d; 1H, CH), 6.52 (d; 1H, CH), 4.65 (s; 2H, —CH₂—), 2.50 (s; 3H, CH₃).

3.3. 2-(Acetylamino)-3-[2'-(5'-methyl)thienylmethyl] propanedioic acid, diethyl ester (12)

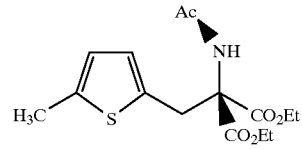

33.6 g (155 mmol) of diethyl acetamidomalonate were added to a solution of 3.56 g (155 mmol) of sodium in 200 ml of anhydrous ethanol at room temperature and the mixture was stirred until a clear solution formed. 29.0 g (152 mmol) of 11 were then added and the mixture was refluxed for 3 h. The solvent was distilled off in vacuo, the residue was taken up in ether/water (3:1) and the aqueous phase was extracted to exhaustion with ether. The combined organic phases were washed with saturated sodium chloride, dried over sodium sulphate and the ether was distilled off.

Crude yield: 50 g

Since the product was contaminated with thiophenemethanol and its decomposition product, the residue was flash-chromatographed on 500 g of silica gel using petroleum ether:ether=1:1.

Yield: 28 g, (55%), m.p.: 98–100° C. $R_f$=0.4651 (petroleum ether:ether=1:2).

$^1$H-NMR (CDCl$_3$): δ=6.75 (bs; 1H, NH), 6.55–6.50 (m; 2H, Th-H-3, -4), 4.25 (q; 2H, OCH$_2$), 3.78 (s; 2H, —CH$_2$—), 2.40 (s; 3H, CH$_3$), 2.05 (s; 3H, acetyl-CH$_3$), 1.30 (t; 6H, CH$_3$).

$^{13}$C-NMR (CDCl$_3$): δ=168.87 (s; CONH), 166.97 (s; COO), 139.22 (S; C), 133.88 (s; C), 126.99 (d; CH), 124.60 (d; CH), 66.83 (s; C), 62.45 (t; OCH$_2$), 32.64 (t; —CH$_2$—), 22.80 (q; CH$_3$), 14.99 (q; CH$_3$), 13.76 (9; CH$_3$).

C$_{15}$H$_{21}$NO$_5$S (327.40): Calculated: C 55.03 H 6.47 N 4.28 Found: C 55.06 H 6.43 N 4.34

3.4. (R,S)-2-(Acetylamino)-3-[(5'-methyl)-2'-thienyl]propanoic acid (13)

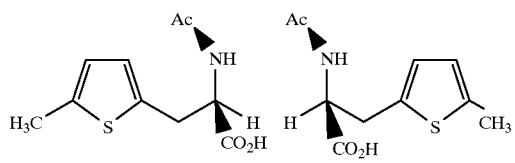

32.9 g (100.5 mmol) of 12 were suspended in 200 ml of 10% strength sodium hydroxide solution and refluxed for 3 h, the solid passing into solution. The solution was then acidified to pH=1 using concentrated hydrochloric acid, with ice cooling, a colourless precipitate forming. The mixture was refluxed again for 3 h.

The reaction solution, after cooling to room temperature, was extracted to exhaustion with ethyl acetate, the combined organic phases were washed with saturated sodium chloride solution and dried with sodium sulphate. The solvent was removed in vacuo, and the residue was dried in vacuo.

Yield: 21.1 g (93% of theory), colourless solid, m.p.: 165–166° C.

$^1$H-NMR (d$_6$DMSO): δ=8.22 (d; 1H, NH), 6.65 (d; 1H, CH), 6.59 (d; 1H, CH), 4.34 (m; 1H, α-CH), 3.15 (dd; 1H, CH of —CH$_2$—), 2.99 (dd; 1H, CH of —CH$_2$—), 2.37 (s; 3H, Ac-CH$_3$), 1.84 (s, 3H, CH$_3$).

$^{13}$C-NMR (d$_6$-DMSO): δ=172.6 (s; COOH), 169.3 (s; CONH), 137.7, (s; C), 137.5 (s; C), 126.0 (d; CH), 124.8 (d; CH), 53.5 (d; α-CH), 31.3 (t; —CH$_2$—), 22.4 (q; Ac-CH$_3$), 14.8 (q; CH$_3$).

C$_{10}$H$_{13}$NO$_3$S (227.29): Calculated: C 52.85 H 5.76 N 6.16 Found: C 52.83 H 5.76 N 6.06

3.5. (S)-2-Amino-[2'-(5'-methyl)thienyl]propanoic acid (14)

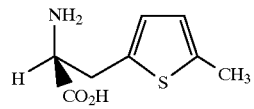

A solution of 13 g (157 mmol) of sodium carbonate and 19.0 g (84.0 mmol) of 13 in 800 ml of water was adjusted to pH 7.5–8 using 2N hydrochloric acid and admixed with 5.0 g of acylase. The suspension was stirred for 24 h at room temperature.

The mixture was then acidified to pH 1–2 using concentrated hydrochloric acid and the denatured enzyme was removed by filtration. The filtrate was exhaustively extracted with ethyl acetate; the combined organic phases were washed with saturated sodium chloride solution and dried with sodium sulphate. After removing the solvent in vacuo, (R)-13 remained as a brownish crystalline powder, which was dried in vacuo.

Yield: 8.9 g (94%), colourless crystalline powder, m.p.: 164° C., $[\alpha]^{23}_D$=−41° (c=1.0, MeOH)

The aqueous phase was evaporated to dryness on a rotary evaporator, taken up in 70 ml of water and added to 250 ml of activated DOWEX 50 ion exchanger. The suspension was stirred for 30 min at room temperature, the ion exchanger was filtered off and washed with water until the eluate was neutral. The ion exchanger was then repeatedly digested with 1M ammonium solution until the filtrate gave a negative ninhydrin test. The combined ammoniacal filtrates were evaporated to dryness in a rotary evaporator in vacuo and the remaining (S)-amino acid was dried in vacuo.

Yield: 7.7 g (100%), brown crystalline powder, m.p.: 252–253° C. $R_f$=0.281 (EtOAc:MeOH=1:1) $[\alpha]^{23}_D$=−3° (c=1.0, 2N HCl ) Literature: m.p.: 253–5° C.

$^1$H-NMR (D$_2$O): δ=6.66 (d; 1H, CH), 6.60 (d; 1H, CH), 3.67 (t; 1H, α-CH), 3.21 (d; 2H, —CH$_2$—), 2.35 (s; 3H, CH$_3$).

$^{13}$C-NMR (D$_2$O): δ=180.4 (s; COOH), 142.7 (s; C), 138.5, (s; C), 129.6.1 (d; CH), 127.7 (d; CH), 58.0 (d; α-CH), 35.5 (t; —CH$_2$—), 16.9 (q; CH$_3$).

3.6. (S)-2-Amino-3-[2-(5-methyl)thienyl]propanoic acid, methyl ester, hydrochloride (15)

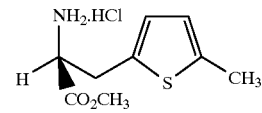

A strong stream of anhydrous hydrogen chloride was passed through a suspension of 3.1 g (16.7 mmol) of 14 into 100 ml of anhydrous methanol for 3 h with vigorous stirring. The reaction mixture was then concentrated to dryness, the residue was taken up in methanol and the solution was admixed with ether. The product precipitated out as a colourless solid, which was filtered off and dried in vacuo.

Yield: 3.8 g (96%), colourless needles, m.p.: 170–172° C. $R_f$=0.739 (EtOAc:MeOH=1:1) $[\alpha]^{23}_D$=+17.5° (c=1.0, MeOH)

$^1$H-NMR (D$_2$O): δ=6.78 (d; 1H, CH), 6.70 (d; 1H, CH), 4.40 (t; 1H, α-CH), 3.44 (d; 2H, —CH$_2$—), 2.40 (s; 3H, CH$_3$).

$^{13}$C-NMR (D$_2$O): δ=172.42 (s; CO), 144.16 (s; C), 134.93, (s; C), 131.26 (d; CH), 128.36 (d; CH), 56.60 (q; OCH$_3$), 56.47 (d; α-CH), 32.56 (t; —CH$_2$—), 17.05 (q; CH$_3$).

C$_9$H$_{14}$ClNO$_2$S.0.25 H$_2$O (240.24): Calculated: C 45.00 H 6.08 N 5.83 Found: C 45.08 H 5.91 N 5.92

3.7. L-β-tert-Butyl-N-carbobenzoxy-α-aspartyl-L-[2-(5-methyl)thienyl]alanine, methyl ester (16)

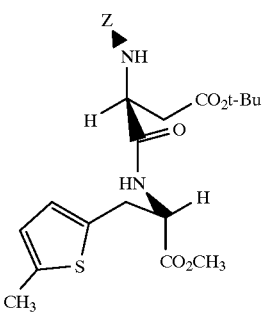

5.50 g (10.9 mmol) of 4 are dissolved in 50 ml of anhydrous DMF and admixed at 0° C. with 2.6 g (10.9 mmol) of 15 and 1.51 ml (10.9 mmol) of triethylamine and stirred at 0–4° C. for 3 days.

The reaction solution was partitioned between 80 ml of ice-water and 50 ml of ether, the aqueous phase was extracted repeatedly with ether and the combined organic phases were washed with saturated sodium chloride solution. The ether solution was dried with sodium sulphate and the solvent was distilled off. The crude product thus obtained was flash-chromatographed on 220 g of silica gel using petroleum ether:ether (gradient from 6:4 to 1:2).

Yield: 4.2 g (76%), colourless solid, m.p.: 56–57° C. $R_f$=0.462 (petroleum ether:ether=1:2), $[\alpha]^{23}_D$=+37.1° (c=1.24, $CH_2Cl_2$)

$^1$H-NMR ($CDCl_3$): δ=7.38–7.33 (m; 5H, $C_6H_5$), 7.08 (bd; 1H, CONH), 6.62 (d; 1H, Th-H), 6.56 (d; 1H, Th-H), 5.97 (d; 1H, CONH), 5.14 (s; 2H, $OCH_2$), 4.80 (m; 1H, α-CH), 4.58 (m; 1H, α-CH), 3.75 (s; 3H, $OCH_3$), 3.27 (m; 2H, —$CH_2$—), 2.90 (dd; 1H, CH of —$CH_2$—), 2.64 (dd; 1H, CH of —$CH_2$—), 2.41 (s; 3H, $CH_3$), 1.44 (s; 9H, $CH_3$).

$^{13}$C-NMR ($CDCl_3$): δ=171.02 (s; CO), 170.91 (s; CO), 170.25 (s; CO), 155.95 (s; CONH), 139.31 (s; C-2-Th), 136.09 (s; C-1-Ph), 134.59 (s; C-5-Th), 128.55 (d; CH), 128.22 (d; CH), 128.05 (d; CH), 126.93 (d; CH), 125.06 (d; CH), 81.80 (s; $OC_{quart}$), 67.20 (t; $OCH_2$), 53.29 (q; $OCH_3$), 52.42 (d; α-CH), 51.04 (d; α-CH), 37.36 (t; —$CH_2$—), 32.09 (t; —$CH_2$—), 27.98 (q; $CH_3$), 15.23 (q; $CH_3$).

3.8. N-L-α-Aspartyl-[2- (5-methyl)thienyl]alanine, methyl ester, hydrobromide (17)

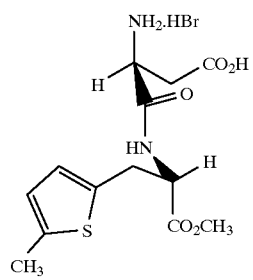

A solution of 4.0 g (7.93 mmol) of 16 in 20 ml of glacial acetic acid was admixed with 11.6 ml (47.6 mmol) of a 4.1M (33%) solution of HBr in glacial acetic acid, dropwise, at room temperature, and the mixture was stirred for 2 h.

The solvents were distilled off in a water-jet vacuum and the oily residue was digested using 100 ml of ether. A colourless crystalline powder precipitated out, which was filtered off and dried in vacuo.

Yield: 3.0 g (96%), of beige crystalline powder, m.p.: 78–79° C. $R_f$=0.387 (EtOAc:MeOH=1:1), $[\alpha]^{25}_D$=+26.7° (c=0.75, HOAc)

$^1$H-NMR ($D_2O$): δ=6.67 (d; 1H, Th-H), 6.62 (d; 1H, Th-H), 4.73 (m; 1H, α-CH), 4.32 (m; 1H, α-CH), 3.71 (s; 3H, $OCH_3$), 3.33 (m; 2H, —$CH_2$—), 3.00 (m; 2H, —$CH_2$—), 2.37 (s; 3H, $CH_3$).

$^{13}$C-NMR ($D_2O$): δ=175.21 (s; CO), 175.01 (s; CO), 171.04 (s; CO), 142.88 (s; C-2-Th), 138.30 (s; C-5- Th), 129.71 (d; CH), 127.84 (d; CH), 57.14 (d; α-CH), 55.79 (q; $OCH_3$), 52.00 (d; α-CH), 37.48 (t; —$CH_2$—), 33.33 (t; —$CH_2$—), 16.96 (q; $CH_3$).

3.9. Preparation of N-L-α-aspartyl-(L-[2-(5-methyl)thienyl] alanine, methyl ester (3)

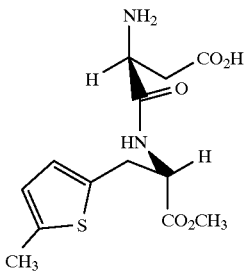

20 ml of strongly basic ion exchanger (Amberlite IRA-400) were stirred in a saturated aqueous sodium acetate solution overnight. The ion exchanger was then filtered off and washed to neutrality with water.

The Amberlite thus activated was stirred with a solution of 2.80 g (7.10 mmol) of 17 in 50 ml of water at 45° C. for 30 min. The solid was filtered off, washed with 30 ml of water and the eluate and the washing solutions were highly concentrated in vacuo. On cooling, colourless needles precipitated out, which were filtered off and dried.

Yield: 1.6 g (72%), colourless needles, m.p.: 234–235° C. $R_f$=0.428 (EtOAc:MeOH=1:1), $[\alpha]^{25}_D$=+45° (c=0.75, HOAc)

$^1$H-NMR ($D_2O$): δ=6.68 (d; 1H, Th-H), 6.63 (d; 1H, Th-H), 4.67 (m; 1H, α-CH), 4.19 (m; 1H, α-CH), 3.72 (s; 3H, $OCH_3$), 3.32 (dd; 1H, CH of —$CH_2$—), 3.22 (dd; 1H, CH of —$CH_2$—), 2.75 (dd; 1H, CH of —$CH_2$—), 2.63 (dd, 1H, CH of —$CH_2$—Hz).

$^{13}$C-NMR ($D_2O$): δ=178.49 (s; CO), 175.21 (s; CO), 172.09 (s; CO), 142.87 (s; C-2-Th), 138.37 (s; C-5-Th), 129.66 (d; CH), 127.81 (d; CH), 57.03 (d; α-CH), 55.74 (q; $OCH_3$), 53.21 (d; α-CH), 39.62 (t; —$CH_2$—), 33.45 (t; —$CH_2$—), 16.90 (q; $CH_3$).

What is claimed is:

1. L-aspartyl-L-thienylalanine methyl ester of the formula

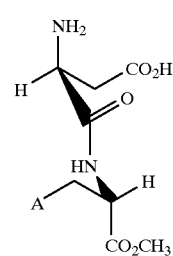

I where A is a radical of the formula

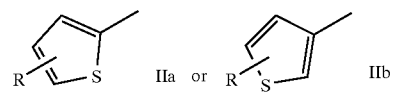

in which R can be H or $CH_3$.

2. Compound of the formula I, according to claim 1, characterized in that A is 2'-thienyl, 3'-thienyl or 2'-(5'-methyl)thienyl.

3. Process for preparing compounds of the formula

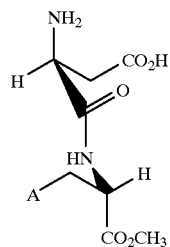   I where A is a radical of the formula

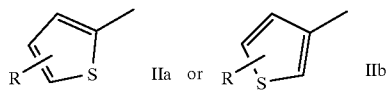

in which R can be H or CH$_3$, which is characterized in that a compound of the formula

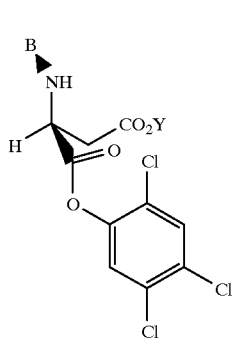   III where B is an amino protecting group and Y is a carboxyl protecting group, is reacted with a compound of the formula

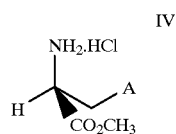   IV where A has the above meaning, in the presence of an acid acceptor, to give a compound of the formula

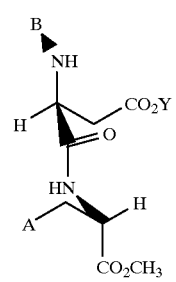   V where A, B and Y have the above meaning, whereupon, after removing protecting groups by the acidolytic method, the corresponding compound of the formula I is isolated using a base from the salt thus produced.

4. A process for using compounds of the formula

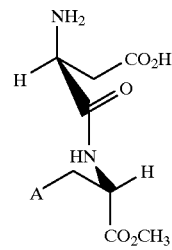   I where A is a radical of the formula

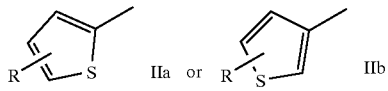

in which R can be H or CH$_3$, as artificial sweetener.

* * * * *